United States Patent [19]

Hoppe et al.

[11] Patent Number: 4,496,723

[45] Date of Patent: Jan. 29, 1985

[54] PROCESS FOR THE PREPARATION OF 7-AMINO-1-DETHIA-1-OXA-3-HYDROXYMETHYL-CEPHEM-4-CARBOXYLIC ACIDS

[75] Inventors: Dieter Hoppe; Heinz-Werner Kleemann, both of Goettingen, Fed. Rep. of Germany

[73] Assignee: Bayer Aktiengesellschaft, Leverkusen, Fed. Rep. of Germany

[21] Appl. No.: 506,731

[22] Filed: Jun. 20, 1983

[30] Foreign Application Priority Data

Jul. 6, 1982 [DE] Fed. Rep. of Germany ....... 3225269

[51] Int. Cl.$^3$ ........................................... C07D 498/04
[52] U.S. Cl. ................................... 544/90; 260/245.5; 260/330.9; 544/95; 544/374; 546/275; 548/147; 549/273
[58] Field of Search ......................... 260/245.5, 330.9; 544/90, 95, 374; 546/275; 548/147; 549/273

[56] References Cited

PUBLICATIONS

Narisada et al., J. Antibiotics, vol. 35 (1982) p. 463.

*Primary Examiner*—Richard L. Raymond
*Attorney, Agent, or Firm*—Sprung, Horn, Kramer & Woods

[57] ABSTRACT

Compounds which themselves are antibacterially active and/or which are useful as intermediates for producing antibacterially active materials such as penicillins and cephalosporins are obtained by the following syntheses:

Benzyl-2-(2,2-dimethyl-1,3-dioxan-5-ylidene)-2(N-formyl-1)-aminoacetate to benzyl-2,2-dimethylspiro-[1,3-dioxane-5,5'-1',3-thiazoline]-4'-carboxylate to benzyl 2-(2,2-dimethyl-1,3-dioxan-5-ylidene)-2[N-(methylthiomethylene)-amino] acetate to benzyl 2-(trans-3-azido-4-methylthio-2-oxo-1-azetidinyl)-2-(2,2-dimethyl-1,3-dioxan-5-ylidene) acetate to benzyl 2(trans-3-benzoylamino-4-methylthio-1-azetidinyl)-2-(2,2-dimethyl-1,3-dioxan-5-ylidene) acetate to either (1) benzyl 2-(7-oxo-3-phenyl-4-oxa-2,6-diazabicyclo[3.2.0]hept-2-en-6-yl)-2-(2,2-dimethyl-1.3-dioxan-5-ylidene)acetate or (2) benzyl 2-(trans-3-benzoylamino-4-chloro-1-azetidinyl)-2-(2,2-dimethyl-1,3-dioxan-5-ylidene) acetate and then to the product benzyl-7-benzoylamino-1-dethia-1-oxa-3-hydroxymethyl-cephem-4-carboxylate.

5 Claims, No Drawings

PROCESS FOR THE PREPARATION OF 7-AMINO-1-DETHIA-1-OXA-3-HYDROXYMETHYL-CEPHEM-4-CARBOXYLIC ACIDS

The present invention relates to a new process for the preparation of 7-amino-1-dethia-1-oxa-3-hydroxymethyl-cephem-4-carboxylic acids and to their use as antibacterial agents and for the preparation of antibacterial derivatives of 7-amino-1-dethia-1-oxa-3-hydroxymethyl-cephem-4-carboxylic acids.

It has already been disclosed that 7-amino-1-dethia-1-oxa-3-hydroxymethyl-cephem-4-carboxylic acids can be synthesized from 3-azido-4-methylthio-azetidinone-1-α-phosphonoacetic acid by chlorination, substitution with monoacetyl-1,3-dihydroxyacetone and subsequent Wittig reaction and reduction of the azido group (Merck, DOS [German Published Specification No.] 2,355,209, 6.11.1972; Cama and Christensen, J.Am.Chem.Soc., 96, 7582 (1974); Yoshioka et al., Tetrahedron Letters 1979, 4287; Uyeo et al., J.Am.Chem.Soc. 101, 4403 (1979)), but in this process the hydrogenated oxazine ring system which is fused to the azetidinone ring system has to be synthesized in three stages, because the ring fragment 1-3 has to be introduced in two stages into the pre-prepared azetidinone ring; this is disadvantageous in view of the known sensitivity of the azetidinones.

Furthermore, it has already been disclosed that 7-amino-1-dethia-1-oxa-3-hydroxymethyl-cephem-4-carboxylic acids are obtainable from 3-aminoazetidinone-4-chloro-1-acetic acids or 3,4-oxazolinoazetidinone-1-acetic acids, which carry an isopropenyl or isopropylidene radical at the α-C atom of the acetic acid, and are obtainable from penicillins by ring-opening and desulphurization reactions (Wolfe et al., Can. J. Chem. 52, 3996 (1974); Belgian Patent Specification No. 832,174; Aoki et al., Tetrahedron Letters, 1979, 4327); in this process, however, the side chain on the azetidinone ring has to be oxidized to the desired hydroxymethyl stage (or to its equivalent oxidation stage), and this procedure is difficult to carry out because it has to be effected in the presence of the sensitive 3-amino-substituted azetidinone ring.

A summary of the prior art is given by M. Narisada et al., J. Antibiotics, 35, 463 (1982).

It has now been found that 7-amino-1-dethia-1-oxa-3-hydroxymethyl-cephem-4-carboxylic acids and their derivatives of the general formula (I),

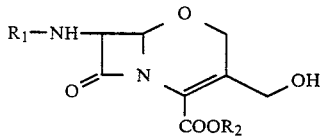

their lactones of the general formula (II)

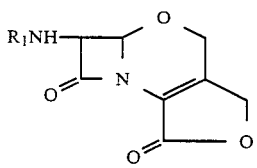

and their double bond isomers of the general formula (III)

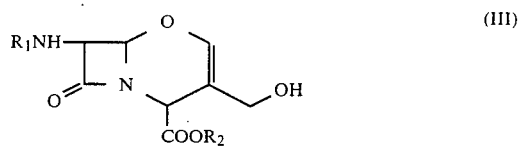

in which $R_1$ is hydrogen or the acyl radical of an organic carboxylic acid, in particular having up to 20 carbon atoms, or the optionally substituted Z protective group (benzyloxycarbonyl), and $R_2$ denotes a carboxyl protective group or a pharmaceutically usable ester radical, are obtained when compounds of the general formula (IV)

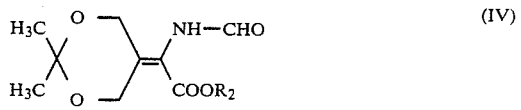

in which $R_2$ has the meaning given above, in a solvent, for example dimethoxyethane, are reacted with a sulphurization agent, for example Lawesson reagent, to give compounds of the general formula (V)

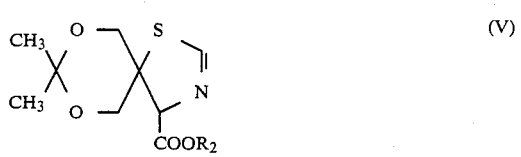

in which $R_2$ has the meaning given above, and these products are then reacted with a strong base, for example butyl-lithium, in a solvent, for example tetrahydrofuran, at low temperatures, for example at $-78°$ C., and then with an alkylating agent, for example methyl iodide, to give compounds of the general formula (VI)

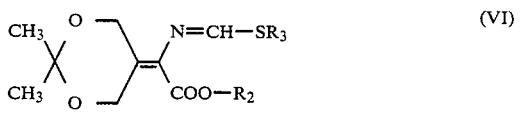

or their double bond isomers of the formula (VI'),

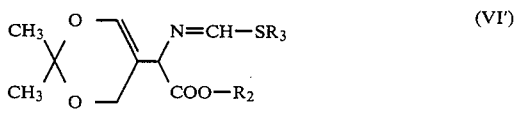

in which $R_2$ has the meaning given above and $R_3$ denotes optionally substituted alkyl, or when compounds of the general formula (IV') or (IV"),

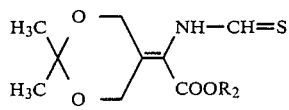 (IV')

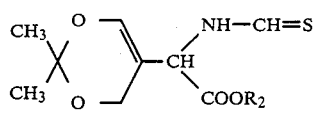 (IV''')

in which
$R_2$ has the meaning given above,
are reacted with an alkylating agent to give compounds of the general formula (VI) or (VI'), these compounds are then reacted with an activated derivative of an acid, for example the acid-chloride, of the general formula (VII)

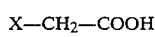 X—CH$_2$—COOH (VII)

in which
X denotes azido or phthalimido,
in the presence of a base, for example triethylamine, in a solvent, for example methylene chloride, to give compounds of the general formula (VIII)

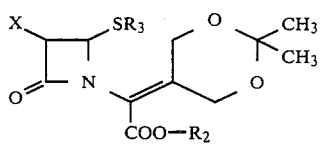 (VIII)

or their double bond isomers of the formula (VIII')

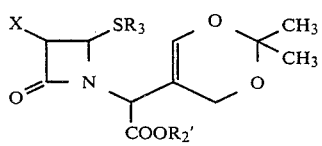 (VIII')

in which
$R_2$, $R_3$ and X have the meaning given above, these compounds, in the case in which X is azido, are then reacted with a reducing agent, for example hydrogen sulphide, in the presence of an amine, for example triethylamine, in a solvent, for example methylene chloride, or, in the case in which X is phthalimido, are reacted with phthalimide-cleaving reagents, for example hydrazine, to give compounds of the general formula (IX)

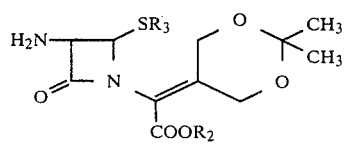 (IX)

or their double bond isomers of the general formula (IX')

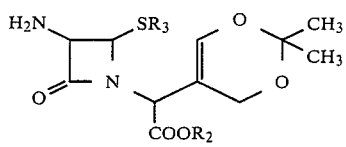 (IX')

in which
$R_2$ and $R_3$ have the meaning given above, these compounds are then reacted with a carboxylic acid $R_1'$—COOH which is activated at the carboxyl group and in which $R_1'$ denotes an organic radical having up to 19 carbon atoms, or these compounds are then reacted with reagents, such as, for example, Z chloride, which are capable of introducing the optionally substituted Z protective group, to give compounds of the general formula (X)

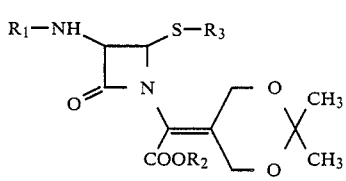 (X)

or their double bond isomers of the general formula (X')

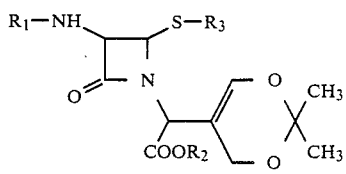 (X')

in which
$R_1$, $R_2$ and $R_3$ have the meaning given above, and the compounds of the general formula X are then reacted with a chlorinating agent, such as chlorine or sulphuryl chloride, in a solvent which is inert to chlorination, such as chloroform or ethyl acetate, and are then reacted with a protic acid, such as trifluoroacetic acid, or with a Lewis acid, such as BF$_3$, in the same solvent, to give compounds of the general formula (I) or (II), and the compounds of the general formula (X') are reacted with a chlorinating agent, such as chlorine or sulphuryl chloride, in a solvent which is inert to chlorination, such as chloroform or ethyl acetate, and are then reacted with a protic acid, such as trifluoroacetic acid, or with a Lewis acid, such as BF$_3$, to give compounds of the general formula (III)

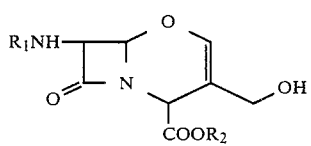 (III)

in which
$R_1$ and $R_2$ have the meaning given above.
The conversion of the compound of the general formula (X) or (X') to the compounds of the general formula (I), (II) or (III) can also be carried out by reaction with a chlorinating agent, such as chlorine or sulphuryl chloride, in a solvent which is inert to chlorination, such as chloroform or ethyl acetate, followed by working-up in an aqueous medium at pH 7 to give intermediate products of the general formula (XI) or their double bond isomers of the general formula (XI'),

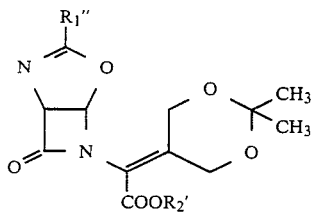     (XI)

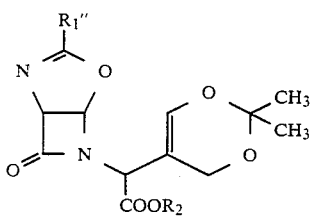     (XI')

in which $R_2$ has the meaning given above and $R_1''$ has the meaning of $R_1'$ and additionally denotes optionally substituted benzyloxy, and further reaction of these with protic acids, such as trifluoroacetic acid, or Lewis acids, such as boron trifluoride.

It is to be regarded as extremely surprising that, in accordance with the reaction sequence according to the invention, the synthesis of the 7-amino-1-dethia-1-oxa-3-hydroxymethyl-cephem-4-carboxylic acid system takes place without oxidation reactions of the intact azetidinone ring system being carried out, and that the fused hydrogenated oxazine ring system is synthesized in a two-stage procedure, since it was to be expected that a synthesis of this type could take place only with the aid of oxidation reactions of the intact azetidinone ring system, or by synthesizing the fused hydrogenated ring system in at least three stages.

The process according to the invention has a number of advantages. Thus, for example, in order to obtain the compounds of the general formulae (I), (II) and (III), it is not necessary to link further framework and substituent atoms to the intact azetidinone ring, since all framework and substituent atoms have already been introduced when the azetidinone ring was linked, and only simple reduction, substitution or elimination reactions are still required, which, moreover, take place with excellent yields.

If the compound (XII) is used as a starting material, the course of the reaction can be represented by the following equation:

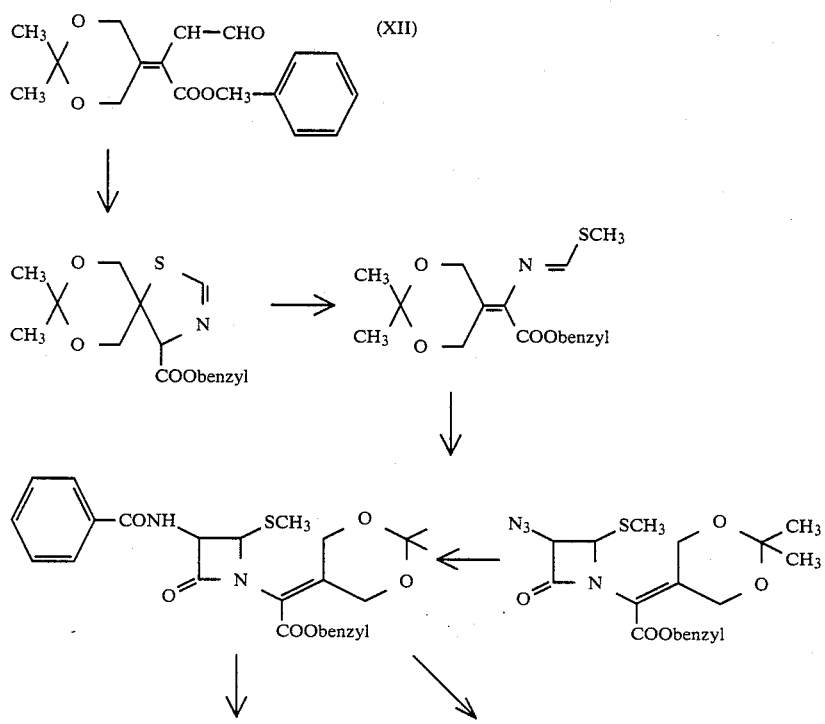

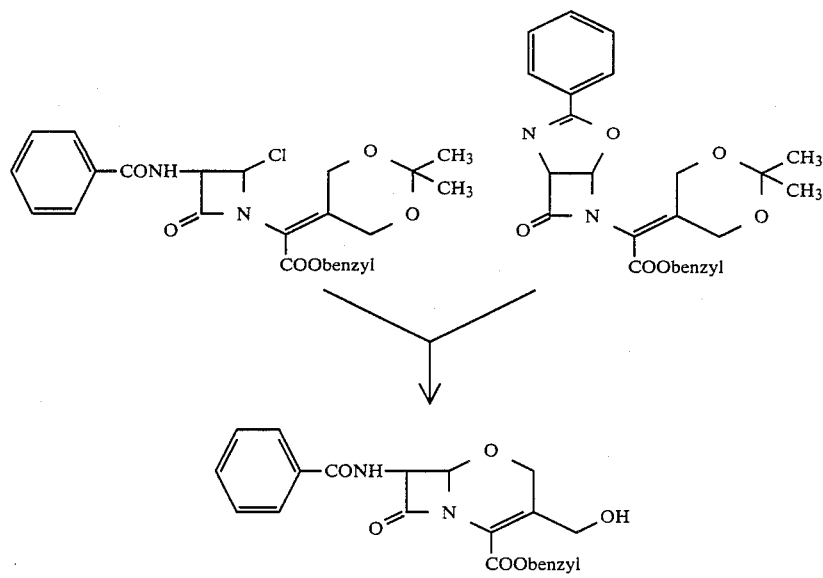

In the general formula (IV), $R_2$ preferably represents benzhydryl or benzyl which is optionally substituted by methoxy or nitro, or represents 1-ethoxy-carbonyloxyethyl, pivaloyloxymethyl, acetoxymethyl, phthalidyl, β-trimethylsilylethyl, β-halogenoethyl or β-trichloroethyl, or a similar protective group which can be split off by β-elimination.

The compounds (IV) are acetone acetals; almost any other ketones may of course also be employed for acetal formation; aldehydes can also be employed as reactants in the acetalization process.

The preparation of the compounds (IV), (IV') and (IV'') is described in the examples or can be carried out in an analogous manner. In the general formulae (VI) and (VI'), $R_3$ denotes an alkyl radical which has up to 5 carbon atoms and is optionally substituted by an ester group or a carbonyl group. Since this radical is split off again in the reaction sequence according to the invention, many other radicals apart from the stated radicals $R_3$ can of course also be employed.

In the general formulae (X) and (X'), $R_1$ preferably denotes the Z protective group or the radical $R_1'$—CO— of a carboxylic acid, wherein $R_1'$ preferably corresponds to the radicals (1) to (17), and the aryl groups occurring in the radicals can be substituted by one or two methoxy, hydroxyl, amino or aminomethyl groups, which in turn can be acylated by acetyl, propionyl, methoxycarbonyl, ethoxycarbonyl or—in the case of amino groups—mesyl or sulpho groups, and aliphatic and heterocyclic carboxyl and amino groups should be protected by protective groups, such as benzyl, benzhydryl, trimethylsilylethyl or Z-, BOC-, trityl or cyanoethoxycarbonyl.

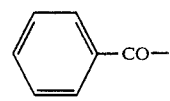

(1)

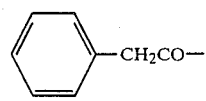

(2)

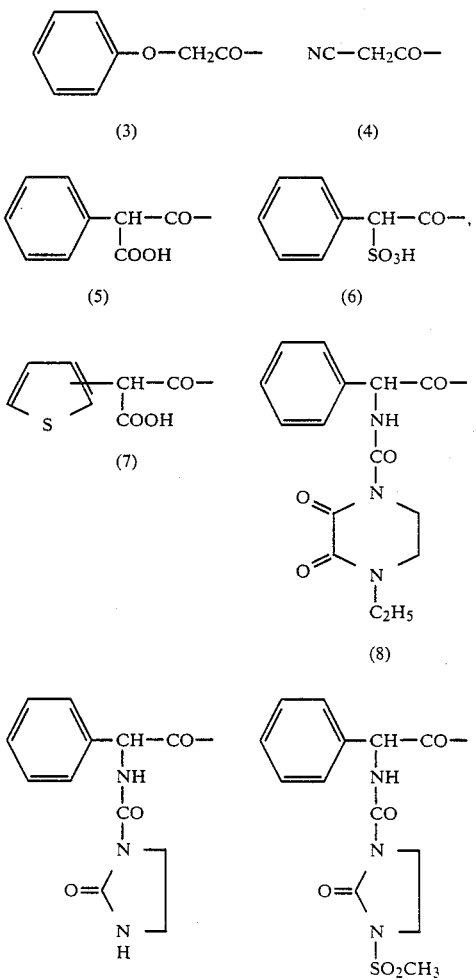

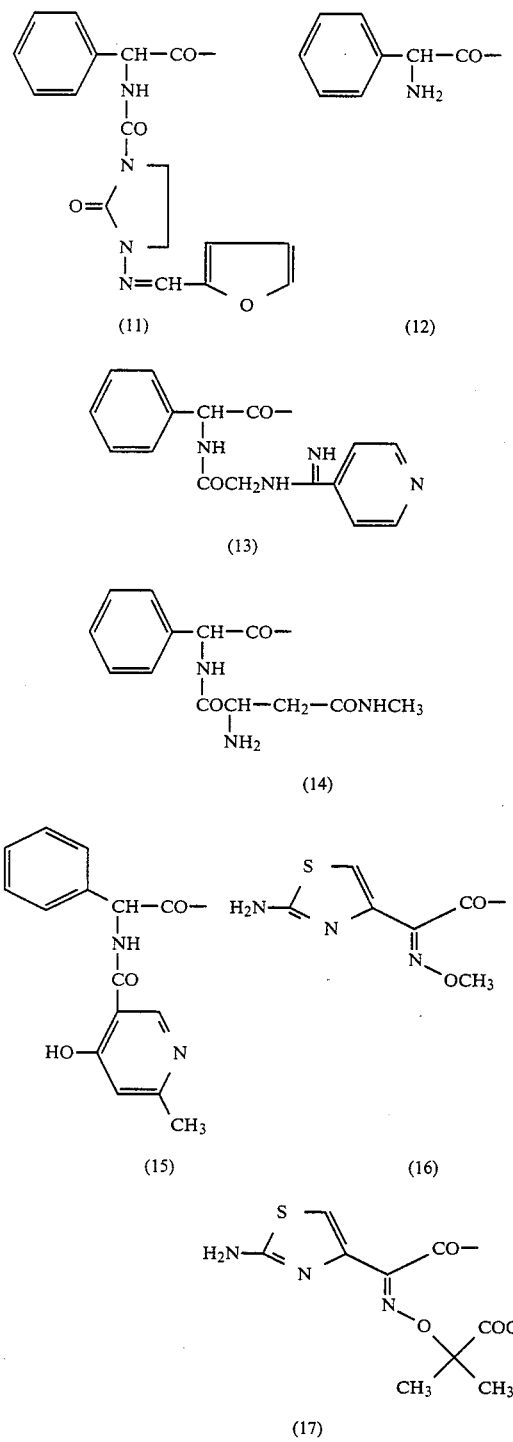

(11) (12) (13) (14) (15) (16) (17)

In the preparation, according to the invention, of the compounds of the general formula (V) from the compounds of the general formula (IV), examples of suitable diluents are dimethoxyethane, diglyme, triglyme, tetrahydrofuran, dioxane, diethyl ether, t-butyl methyl ether, dichloromethane, carbon tetrachloride, 1,2-dichloroethane, 1,1,2-trichloroethane, trichloroethylene, chlorobenzene, dichlorobenzene, chloroform, ethyl acetate, aniline, piperidine, toluene, cyclohexane, acetonitrile and nitromethane, and examples of suitable sulphurization agents are 2,4-bis-(4-methoxyphenyl)-2,4-dithioxo-1,3,2,4-dithiadi-phosphetane (Lawesson reagent), 2,4-bis-(4-chlorophenyl)-2,4-dithioxo-1,3,2,4-dithiadiphosphetane, 2,4-diphenyl-2,4-dithioxo-1,3,2,4-dithiadiphosphetane, phosphorus pentasulphide, phosphorus trisulphide, disulphur tetranitride, tetrasulphur tetranitride, trithiazyl chloride, elementary sulphur and polysulphur dichloride.

In the preparation, according to the invention, of the compounds of the general formula (VI) or (VI') from the compounds of the general formula (V), examples of strong bases, in addition to butyl-lithium, are phenyl-lithium, lithium diisopropylamide, lithium hexamethyl-disilazanide, potassium tert.-butylate, sodium amide, potassium dimethylsulphoxide, lithium hydroxide, sodium methylate, sodium carbonate and potassium carbonate, and examples of suitable diluents, in addition to tetrahydrofuran, are dioxane, dimethoxyethane, ammonia, dimethylsulphoxide, methanol, hexamethylphosphoric acid triamide and dimethylformamide, and examples of suitable alkylating agents, in addition to methyl iodide, are dimethyl sulphate, methyl sulphonate, methyl trifluoromethanesulphonate, trimethyloxonium tetrafluoroborate, allyl bromide, benzyl bromide and isopropyl iodide. The same alkylating agents are suitable for the conversion, according to the invention, of the compounds of the general formula (IV') or (IV'') to the compounds of the general formula (VI) or (VI').

The reaction is carried out at temperatures of $-78°$ C. to $+40°$ C.

In the preparation, according to the invention, of the compounds of the general formula (VIII) or (VIII') from compounds of the general formula (VI) or (VI'), examples of suitable diluents, in addition to dichloromethane, are dicloroethane, chlorobenzene, toluene, chloroform, ethyl acetate, tetrahydrofuran, dioxane and diethyl ether, and examples of suitable bases, in addition to triethylamine, are piperidine, N-methylmorpholine, picolone, lutidine, potassium carbonate, NaOH and phase-transfer reagents, such as, for example, crown ethers.

The reaction is carried out at temperatures of $-40°$ to $+60°$ C.

In the preparation, according to the invention, of the compounds of the general formula (IX) or (IX') from compounds of the general formula (VIII) or (VIII'), in which X denotes azido, examples of suitable reducing agents, in addition to hydrogen sulphide/pyridine, are hydrogen/palladium/charcoal, hydrogen/platinum, zinc/glacial acetic acid and tin(II) chloride/glacial acetic acid, and, when X denotes phthalimide, examples of suitable imide-cleaving reagents, in addition to hydrazine, are substituted hydrazines, and examples of suitable diluents are water, dichloromethane, dimethylformamide, chlorobenzene, toluene, ethyl acetate, tetrahydrofuran, ethanol and glacial acetic acid.

The reaction is carried out at temperatures of $-30°$ to $+90°$ C.

In the preparation, according to the invention, of the compounds of the general formula X or X' from compounds of the general formula (IX), examples of suitable diluents are water, acetonitrile, dichloromethane, dichloroethane, chlorobenzene, tetrahydrofuran, dimethylformamide, hexamethylphosphoric acid triamide, dimethylsulphoxide, nitrobenzene, nitromethane and sulpholane and, in the case in which bases are added owing to the liberation of acids from the activated carboxylic acid $R_1'$—COOH or from the Z-group-introducing reagent, examples of suitable bases are sodium hydroxide solution, sodium bicarbonate, pyridine, piperidine, picoline, N-methylmorpholine, diisopropylamine, triethylamine, 4-dimethylaminopyridine, polyvinylpyridine or basic ion exchangers.

The reaction is carried out at temperatures of −80° C. to +60° C. Examples of suitable carboxyl-activated carboxylic acids R'—COOH in this reaction, in protected or unprotected form, are acids of the following formulae:

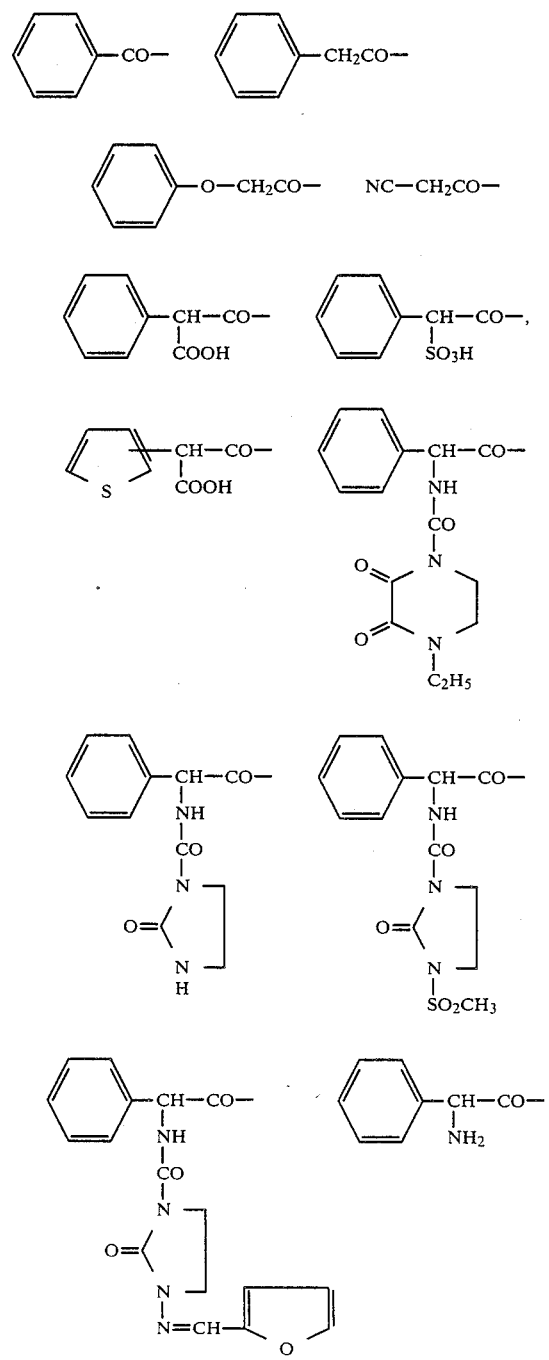

-continued

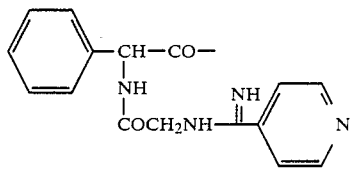

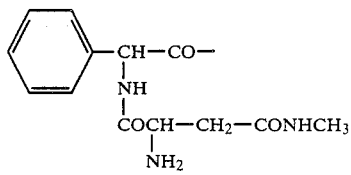

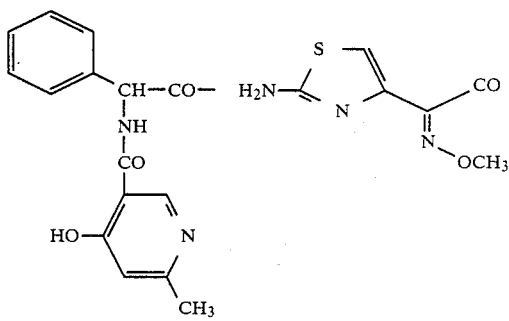

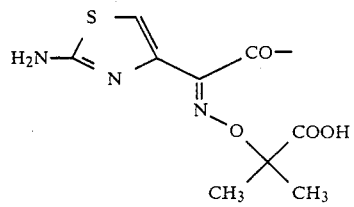

To activate the carboxylic acids R'—COOH, all activating methods customarily used in peptide or β-lactam antibiotic chemistry are suitable, such as, for example, the acid-chloride, carbodiimide, mixed anhydride or activated ester method.

In the preparation, according to the invention, of the compounds of the general formula (I), (II) or (III) from compounds of the general formula (X), examples of suitable chlorinating agents, in addition to chlorine or sulphuryl chloride, are N-chlorosuccinimide, trichloroisocyanuric acid and chlorosulphonic acid, in a diluent which is inert to chlorination, such as, for example, dichlorobenzene, glacial acetic acid, nitrobenzene, carbon tetrachloride, chloroform, ethyl acetate, dichloromethane or tert.-butyl methyl ether. The chlorination step is carried out at temperatures of −80° to +100° C. For cyclization to obtain the compounds of the general formulae (I) and (II) from the chlorinated compounds of the general formula (X), and to obtain (III) from (X'), examples of suitable protic acids are trifluoroacetic acid, trifluoromethanesulphonic acid, perchloric acid, tetrafluoroboric acid, hydrochloric acid, 3,4-dihydroxycyclobut-3-ene-1,2-dione, p-toluenesulphonic acid, camphorsulphonic acid and polyphosphoric acid, and examples of suitable Lewis acids are boron trifluoride, zinc(II) chloride, aluminum chloride, tin(IV) chloride, mercury(II) chloride, silicon tetrachloride, trimethylsilyl trifluoromethanesulphonate and trimethylsilyl trifluoroacetate, and examples of suitable diluents are the diluents of the chlorinating step. In the preparation, according to the invention, of the compounds of the general formula (XI) or (XI') from the chlorination products of the compounds of the general formula (X) or (X'), a suitable working-up procedure, instead of the aqueous working-up at about pH 7, is, for example, working up with sodium bicarbonate solution or disodium hydrogen phosphate solution, or contact with silica gel or basic aluminum oxide.

A conversion of the products of the general formulae (I), (II) and (III) into one another and into other known 7-amino-1-dethia-1-oxa-3-methyl-cephem-4-carboxylic acids which are substituted at the methyl group by radicals other than the OH group is summarized by M. Narisada et al., J. Antibiotics, 35, 463 (1982).

EXAMPLE 1

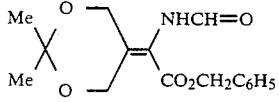

Benzyl 2-(2,2-dimethyl-1,3-dioxan-5-ylidene)-2-(N-formyl)-aminoacetate 14.0 g (80 millimols) of benzyl isocyanoacetate (dissolved in 60 ml of tetrahydrofuran) were added dropwise to 10.0 g (80 millimols) of 90% strength potassium tert.-butylate in 50 ml of anhydrous tetrahydrofuran under $N_2$ at $-60°$ C., the mixture was stirred for 10 minutes at this temperature and 10.4 g (80 millimols) of 2,2-dimethyl-1,3-dioxan-5-one (in 40 ml of tetrahydrofuran) were added dropwise. Stirring was continued (30 minutes at $-60°$ C. and 30 minutes at 0° C.), and the reaction mixture was neutralized with 4.8 g (80 millimols) of acetic acid in 200 ml of dichloromethane. The mixture was washed with water ($3 \times 100$ ml) and dried over sodium sulphate, and the solvent was removed in vacuo. 19.8 g (81%) of product of melting point 80° C. were obtained.

IR (KBr): 333 (NH), 1743 (OC=O), 1698, 1671, 1517 (NHC=O), 1646 cm$^{-1}$ (C=C).

$^1$H—NMR (CDCl$_3$, $\delta$): 1.31 (s, 2 CH$_3$), 4.16 and 4.38 (each s, OCH$_2$), 5.13 (s) and 7.3 (m) (CH$_2$C$_6$H$_5$), 7.60 and 8.06 (each broad s., NHCH=O).

EXAMPLE 2

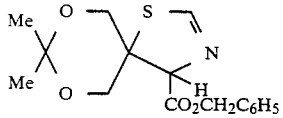

Benzyl 2,2-dimethyl-spiro-[1,3-dioxane-5,5'-1',3'-thiazoline]-4'-carboxylate 3.66 g (12.0 millimols) of benzyl 2-(2,2-dimethyl-1,3-dioxan-5-ylidene)-2-N-formylamino)-acetate (Example 1) in 37 ml of anhydrous and peroxide-free 1,2-dimethoxyethane were stirred with 2.91 g (7.2 millimols) of 2,4-bis-(4-methoxyphenyl)-2,4-dithioxo-1,3,2,4-dithiadiphosphetane (Lawesson reagent)*) for 20 minutes at 20° C. (monitoring by thin-layer chromatography). The reaction mixture was stirred in 120 ml of saturated aqueous sodium bicarbonate solution, and the solution was extracted with three times 50 ml of tert.-butyl methyl ether. Drying the organic phase and removing the solvent in vacuo gave 3.76 g (98%) of pale yellow oil.

*)It was found that the reaction did not begin when some charges of commercial or self-prepared Lawesson reagent were used. In these cases, it could be "activated" by flushing it for a short time, in the absence of moisture, with 30 times its volume of 1,2-dimethoxyethane (cooled to $-20°$ C.).

IR (KBr pellet): 1743 (C=O), 1580 cm$^{-1}$ (C=N)

$^1$H—NMR (CDCl$_3$): $\delta = 1.27$ and 1.38 (each s, 2 CH$_3$), 3.78, 3.87, 3.95 and 4.08 (AB parts; 2 CH$_2$), 4.73 (d, J=1.8 Hz; C—4—H), 5.24 (s; CH$_2$Ph), 7.37 (s; C$_6$H$_5$), 8.07 (d, J=1.8 Hz; C—2—H).

EXAMPLE 3

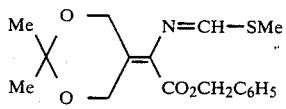

Benzyl 2-(2,2-dimethyl-1,3-dioxan-5-ylidene)-2-[N-(methylthiomethylene)-amino] acetate 0.50 ml of a 1.55N solution (0.77 millimol) of n-butyllithium in hexane was added to 230 mg (0.72 mmol) of the unpurified thiazoline (from Example 2), dissolved in 4 ml of anhydrous tetrahydrofuran, under $N_2$ at $-78°$ C., and the mixture was stirred for 15 minutes at this temperature. Thereafter, 0.47 ml (0.75 millimol) of methyl iodide was added, and the mixture was stirred for 1 hour at $-30°$ C. and for 3 hours at 0° C. The reaction mixture was filtered through a glass frit which was covered with 1 cm of kieselguhr. After the solvent had been stripped off in vacuo, 150 mg (62%) of dark oil were obtained from the filtrate. IR (KBr pellet): 1713 (C=O), 1588 cm$^{-1}$ (C=N). $^1$H—NMR (CDCl$_3$): $\delta = 1.41$ (s; 2CH$_3$), 2.40 (s; SCH$_3$), 4.53 and 4.67 (each s, 2CH$_2$), 5.22 (s; CH$_2$Ph), 7.36 (s; C$_6$H$_5$), 8.56 (s; N=C—H),

EXAMPLE 4

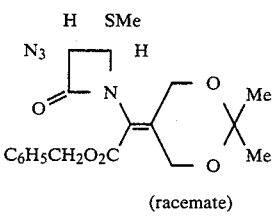

(racemate)

Benzyl 2-(trans-3-azido-4-methylthio-2-oxo-1-azetidinyl)-2-(2,2-dimethyl-1,3-dioxan-5-ylidene) acetate 0.68 g (5.77 millimols) of azidoacetyl chloride in 10 ml of dichloromethane was added dropwise, in the course of 90 minutes, at 20° C., to a stirred solution of 1.29 g (3.85 millimols) of the unpurified product from Example 3 and of 0.80 ml (5.77 millimols) of triethylamine in 90 ml of anhydrous dichloromethane. The mixture was stirred for a further 30 minutes, the solvent was stripped off in vacuo at room temperature, the residue was taken up with 90 ml of toluene, the solution was filtered off from the precipitated salts, the solvent was stripped off in vacuo and the residue was chromatographed over 50 g of silica gel with diethyl ether/petroleum ether (1:1), $R_f=0.35$. 1.35 g (84%) of product of melting point 74° C. (from petroleum ether) were obtained.

$C_{19}H_{22}N_4O_5S$ (418.47) Calculated: C 54.53 H 5.30. Found: C 54.70 H 4.38.

IR (KBr): 2100 ($N_3$), 1775 (C=O=lactam), 1718 (C=O=ester), 1625 and 1640 cm$^{-1}$ (C=O)

$^1$H—NMR (CDCl$_3$): $\delta = 1.40$ (s; 2 CH$_3$), 1.98 (s; SCH$_3$), 4.18 (AB part, $J_{AB}=16.0$ Hz; CH$_2$O trans to the carboxyl group), 4.44 (d, J=2.3 Hz; C——H), 4.48 (AB part, d, $J_{AB}=16.0$ Hz, J=1.7 Hz; CH$_2$O trans to the ester group), 4.73 (AB part, d, J=1.7 Hz; CH$_2$O cis to the ester group), 4.78 (AB part, s; CH$_2$O cis to the ester group), 4.98 (d, J=2.3 Hz; C—4—H), 5.12 and 5.36 (AB, $J_{AB}=11.8$ Hz; CH$_2$-benzyl), 7.37 (s; C$_6$H$_5$).

EXAMPLE 5

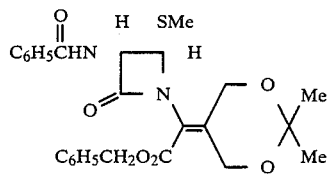

Benzyl 2-(trans-3-benzoylamino-4-methylthio-1-azetidinyl)-2-(2,2-dimethyl-1,3-dioxan-5-ylidene) acetate Hydrogen sulphide was passed into a solution of 0.64 g 1.53 millimols) of the product of Example 4 and 0.32 ml of triethylamine in 16 ml of dichloromethane at 0° C. until azide (2,100 cm$^{-1}$) was no longer detectable in the IR spectrum of a sample (1.5 hours). The solvent was removed in vacuo, the residue was taken up in 65 ml of anhydrous chloroform, 0.26 ml (3.2 millimols) of pyridine were added and a chloroform solution of 0.38 ml (0.32 millimol) of benzoyl chloride was then added dropwise at −5° C. The reaction mixture was stirred for 1 hour at 20° C., then extracted by shaking with three times 30 ml of phophate buffer (pH 7) and dried over sodium sulphate, and the solvent was then removed in vacuo.

Chromatographing the residue over silica gel (50 g) with tert.-butyl methyl ether/petroleum ether (1:1) gave 0.61 g (80%) of product of melting point 67° C. (from tert.-butyl methyl ether).

IR (KBr): 3360 (NH), 1773 (C=O-lactam), 1720 (C=O-ester), 1668 and 1535 cm$^{-1}$ (C=O-amide).

$^1$H—NMR (CDCl$_3$): $\delta = 1.42$ (s; 2 CH$_3$), 2.07 (s; SCH$_3$), 4.26 and 4.55 (AB, $J_{AB}=16.5$ Hz; CH$_2$O), 4.66 and 4.90 (AB, $J_{AB}=17.5$ Hz; CH$_2$O), 5.15 (dd, $J_1=7.7$ Hz; $J_2=2.5$ Hz, C——H), 5.24 (d, J=2.5 Hz; C—4—H), 5.18 and 5.35 (AB, $J_{AB}=11.8$ Hz; CH$_2$-benzyl), 7.30-7.00 (m; NH, aromatic H).

$^{13}$C—NMR (CDCl$_3$): $\delta = 12.4$ (SCH$_3$), 23.7 and 23.9 (2 CH$_3$), 61.0 and 61.3 (2CH$_2$O), 62.4 (C—3), 68.0 (CH$_2$-benzyl), 68.2 (C—4), 100.8 (acetonide—C—2), 115.7 (=C), 123.7, 128.8, 129.0, 132.3, 133.1 and 135.3 (aromatic C), 155.2 (N—C=), 162.6, 163.8 and 167.7 (C=O).

EXAMPLE 6

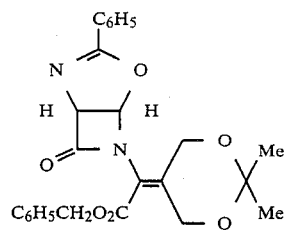

Benzyl 2-(7-oxo-3-phenyl-4oxa-2,6-diazabicyclo[3.2.0]hept-2-en-6-yl)-2-(2,2-dimethyl-1,3-dioxan-5-ylidene) acetate (5)

0.75 ml (0.22 millimol) of a 0.3M solution of chlorine in carbon tetrachloride was added to 106 mg (0.22 millimol) of the product from Example 5 in 5 ml of dry chloroform, under N$_2$, at −40° C. After 15 minutes, the mixture was warmed up to −15° C. and stirred for a further 3 hours at this temperature, and the solvent and the volatile by-products were then stripped off in vacuo—in the final stage at 10$^{-4}$ mm Hg— at −15° C. (approx. 4 hours). 6 ml of acetone (cooled to −15° C.) and then 6 ml of phosphate buffer (pH 7) were added to the residue, and the mixture was stirred for a further hour at 20° C. It was then extracted with dichloromethane (3 × 10 ml), and the extracts were dried over sodium sulphate and sodium bicarbonate. The crude product which remained after the solvent had been stripped off in vacuo was chromatographed over silica gel (neutral, 8 g) with tert.-butyl methyl ether/petroleum ether (1:1). 71 mg (72% of product ($R_f=0.25$) of melting point 51° C. were obtained (from the mixture used for chromatography).

IR (KBr): 1784 (C=O—Lactam), 1720 (C=O—ester) and 1635 cm$^{-1}$ (C=N).

$^1$H—NMR (CDCl$_3$, $\delta$): 1.30 (s, 2CH$_3$), 3.88 and 4.30, 4.63 and 4.67 (each AB part, each OCH$_2$), 5.02 and 5.23 (AB, J=12 Hz, OCH$_2$PH), 7.25-7.45 and 7.80-7.95 (m, C$_6$H$_5$), 5.33 and 6.18 (each d, J=3.5 Hz, $\beta$-lactam protons).

EXAMPLE 7

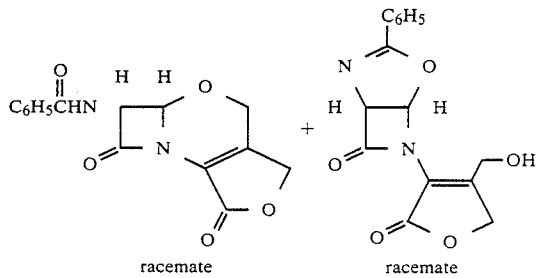

Trans-7-benzoylamino-3-hydroxymethyl-1-oxaceph-3-em-4-carboxylic acid butenolide and
3-(7-oxo-3-phenyl-4-oxa-2,6-diazabicyclo[3.2.0]hept-2-en-6-yl)-4-hydroxymethyl-2,5-dihydrofuran-2-one 24 mg (0.54 millimol) of the product from Example 6 were stirred with 0.4 ml of trifluoroacetic acid for 1 hour at −13° C., under N$_2$. Thereafter, the solvent was stripped off at −10° C. and under 10⁻⁴ mm Hg (1 hour), the residue was taken up with 0.5 ml of dichloromethane, and the solution was chromatographed over 8 g of silica gel with tert.-butyl methyl ether. 9 mg (56%) of a 4:6 mixture of trans-7-benzoylamino-3-hydroxymethyl-1-oxaceph-3-em-4-carboxylic acid butenolide and 3-(7-oxo-3-phenyl-4-oxa-2,6-diazabicyclo[3.2.0]hept-2-en-6-yl)-4-hydroxymethyl-2,5-dihydrofuran-2-one were obtained, and these compounds could be separated by chromatography over silica gel with toluene/tert.-butyl methyl ether (partial decomposition taking place).

Trans-7-benzoylamino-3-hydroxymethyl-1-oxaceph-3-em-4-carboxylic acid butenolide IR (KBr): 1787 (C=O-lactam), 1760 (C=O-butenolide), 1658, and 1530 cm⁻¹ (C=O-amide)

¹H—NMR (CDCl₃, δ): 5.05 (dd, J=2.0 and 7.5 Hz, C—7—H), 6.57 (d, J=2.0 Hz, C—6—H), 4.42 and 4.81 (AB, J=15 Hz, OCH₂-butenolide), 4.93 (s, 2—CH₂), 7.03 (d, J=7.5 Hz, NH), 7.25–8.05 (m, phenyl).

MS: $C_{15}H_{12}N_2O_5$ Calculated 300.0746. Found 300.0746. 3-(7-Oxo-3-phenyl-4-oxa-2,6-diazabicyclo[3.2.0]hept-2-en-6-yl)-4-hydroxymethyl-2,5-dihydrofuran-2-one:

IR (KBr): 1773 (C=O, lactam), 1757 (C=O, butenolide), 1673 (C=C), 1632 cm⁻¹ (C=N).

¹H—NMR (CDCl₃, δ): 2.81 (broad, s, OH), 5.46 and 6.88 (each d, J=3.4 Hz, β-lactam-H), 4.40 and 4.70 (AB, J=15 Hz, OCH₂-butenolide), 4.90 and 4.92 (AB, CH₂—OH), 7.2–8.1 (m, phenyl)

MS: $C_{15}H_{12}N_2O_5$ Calculated 300.0746 Found 300.0746

EXAMPLE 8

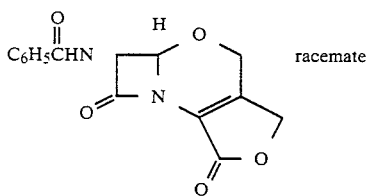

racemate

Trans-7-benzoylamino-3-hydroxymethyl-1-oxaceph-3-em-4-carboxylic acid butenolide 6 from 4

0.14 ml (0.04 millimol) of a 0.3M solution of chlorine in tetrachloromethane was added to 20 mg (0.04 millimol) of the product from Example 5 in 1.5 ml of dry chloroform under N₂, and the mixture was warmed from −40° C. to −15° C., and stirred for 3 hours at this temperature. The volatile constituents were removed in vacuo (under 10⁻⁴ mm Hg in a final stage, 4 hours), the residue was taken up with 0.5 ml of dry deuterochloroform, and 0.1 ml of trifluoroacetic acid was added. After 10 minutes at 20° C., only the title product, in addition to equimolar amounts of acetone and benzyl alcohol, could be detected by ¹H—NMR spectroscopy.

EXAMPLE 9

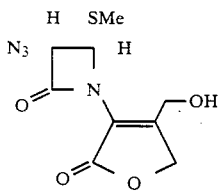

3-Trans-3-azido-4-methylthio-2-oxo-1-azetidinyl)-4-hydroxymethyl-2,5-dihydrofuran-2-one 59 mg (0.14 millimol) of the product from Example 4 in 2 ml of dry dichloromethane were stirred with 19 mg (0.14 millimol) of anhydrous zinc chloride for 12 hours at 20° C. The reaction mixture was chromatographed over 10 g of silica gel with diethyl ether, and gave 13 mg (34%) of 8 ($R_f$=0.23) as a viscous colorless oil.

¹H—NMR (CDCl₃, δ): 2.24 (s, SCH₃), 4.55 (AB, J=16.2 Hz, OCH₂), 4.65 and 4.94 (each d, J=2.6 Hz, C—3— and C—4—H).

IR (CDCl₃): 2103 (N₃), 1770 and 1764 (each C=O) and 1675 cm⁻¹ (C=C).

EXAMPLE 10

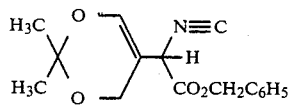

Benzyl 2-(2,2-dimethyl-4,5-dehydro-1,3-dioxan-5-yl)-2-isocyanoacetate 11.0 g (0.72 mol) of phosphorus oxychloride were added dropwise to 19.8 g (0.065 mol) of benzyl 2-(2,2-dimethyl-4,5-dehydro-1,3-dioxan-5-yl)-2-(N-formyl)-aminoacetate (Example 1) and 18.2 g (0.180 mol) of triethylamine in 65 ml of dry dichloromethane at −15° C., while stirring vigorously. The mixture was stirred for 2 hours at 20° C., and then stirred with 65 ml of a 20% strength aqueous K₂CO₃ solution at 15°–20° C. until evolution of CO₂ was no longer observed. After the organic phase had been washed with water (2×65 ml), it was dried and the solvent was stripped off in vacuo. Recrystallization of the residue from diethyl ether/petroleum ether (1:1) gave 11.0 g (61%) of product of melting point 78° C.

IR (CCl₄): 2110 (NC), 1735 (C=O), 1660 cm⁻¹ (O—C=C—). ¹H—NMR (CDCl₃): δ=1.28 and 1.36 (each s; 2CH₃), 3.96 and 4.26 (AB part; CH₂), 4.68 (s; H), 5.13 (s; CH₂-benzyl), 6.56 (s; vinyl-H) 7.23 (s; C₆H₅).

EXAMPLE 11

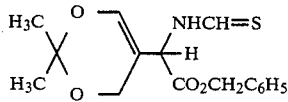

Benzyl 2-(2,2-dimethyl-4,5-dehydro-1,3-dioxan-5-yl)-2-(N-thioformyl)-aminoacetate Hydrogen sulphide was passed into 9.5 g (35 millimols) of the isocyanide from Example 10 and 2 ml of triethylamine in 50 ml of dichloromethane at 10°–20° C. until isocyanide (2,100 cm⁻¹) was no longer detectable in the IR spectrum of a sample (1–2 hours). After 10 ml of toluene had been added, the solvent was stripped off in vacuo, the residue was taken up with 200 ml of ether, and the solution was washed with 1N NaH₂PO₄ solution and then with saturated KCl solution, and dried. After the ether had been stripped off in vacuo, 10.3 g (100%) of the thioformamide remained. An analysis sample was recrystallized from diethyl ether/petroleum ether (1:1) (melting point 89° C.).

IR (KBr pellet): 3290 (NH), 1715 (C=O), 1665 cm$^{-1}$ (=C).

$^1$H—NMR (CCl$_4$): δ=1.35 and 1.38 (each s; 2CH$_3$), 4.11 (s, broad; O—CH$_2$), 5.20 and 5.23 (AB part; CH$_2$-benzyl), 5.52 (d, J=7.0 Hz, H—C—CO$_2$Bz), 6.56 (s, broad; O—CH=), 7.34 (s; C$_6$H$_5$), 8.2–8.4 (s, very broad; NH, undergoes exchange with D$_2$O, 9.42 (d, J=6.0 Hz; CH=S).

C$_{16}$H$_{19}$NO$_4$S (321.39) Calculated C 59.79 H 5.96 S 9.98. Found C 59.65 H 6.03 S 9.97

EXAMPLE 12

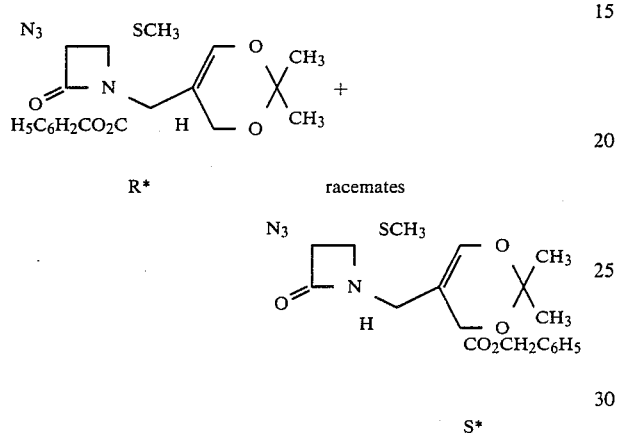

R*                                   racemates

S*

Benzyl 2-(trans-3-azido-4-methylthio-2-oxo-1-azetidinyl)-2-(2,2-dimethyl-4,5-dehydro-1,3-dioxan-5-yl) acetate A solution of 3.0 g (25 millimols) of 90% strength potassium tert.-butylate in 30 ml of tetrahydrofuran was added dropwise to 0.8 g (25 millimols) of the unpurified thioformamide from Example 11 in 30 ml of dry tetrahydrofuran at −78° C., under N$_2$. After 15 minutes, 3.75 g (26 millimols) of methyl iodide were added, and the mixture was warmed to 0° C. and kept at this temperature for 1 hour. The precipitated sodium iodide was filtered off over kieselguhr, under N$_2$, and the solvent was stripped off in vacuo. The yellow oil which remained (8.4 g) was dissolved in 300 ml of dichloromethane (distilled over P$_4$O$_{10}$), 2.0 g (33 millimols) of trimethylamine in dichloromethane were added, and 3.35 g (28 millimols) of azidoacetyl chloride in 50 ml of CH$_2$Cl$_2$ were added dropwise at 20° C. in the course of 5 hours, while stirring vigorously. Thereafter, stirring was continued for 30 minutes, the solvent was stripped off in vacuo, the residue was taken up with 100 ml of benzene, the precipitated hydrochloride was filtered off under suction and the residue was freed from solvent in vacuo. Chromatographing over 1 kg of silica gel with diethyl ether/petroleum ether (1:1) gave 5.0 g (48%) of product as a 1:1 mixture of the diastereomers R* and S* as a pale yellow oil (R*, R$_f$=0.41; S*, R$_f$=0.33). IR (CCl$_4$): 2095 (N$_3$), 1765 (C=O-lactam), 1735 (C=O-ester), 1655 cm$^{-1}$ (C=C).

$^1$H-NMR (CCl$_4$): R* δ=1.37 (s; 2CH$_3$), 1.93 (s; SCH$_3$), 4.14 (s, broad; ring CH$_2$), 4.24 (s; H—C—CO$_2$—Bz), 4.32 (d, J=2.0 Hz; C—3—H), 4.39 (d, J=2.0 Hz; C—4—H), 5.15 (s, broad; CH$_2$-benzyl), 6.34 (s, broad; ring C=CH), 7.29 (s; C$_6$H$_5$). S* δ=1.37 (s; 2CH$_3$), 2.01 (s; SCH$_3$), 4.04 and 4.14 (AB part; ring CH$_2$), 4.24 (s; H—C—CO$_2$—Bz), 4.28 (d, J=2.0 Hz; C—4—H(, 4.51 (d, J=2.0 Hz; C—3—H), 5.15 (s, broad; CH$_2$-benzyl, 6.44 (s, broad; ring C=CH), 7.29 (s; C$_6$H$_5$).

EXAMPLE 13

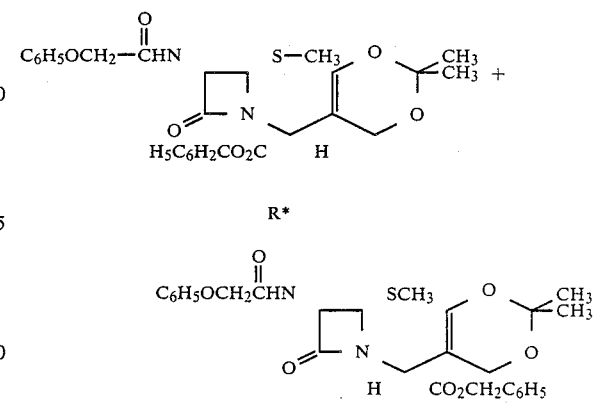

Benzyl 2-(trans-4-methylthio-2-oxo-3-N-phenoxyacetylamino-1-azetidinyl)-2-(2,2-dimethyl-4,5-dehydro-1,3-dioxan-5-yl) acetate A stream of hydrogen sulphide was passed into a solution of 2.44 g (5.8 millimols) of the azide from Example 12 and 0.96 ml (6.9 millimols) of triethylamine in 60 ml of dichloromethane at 0° C. until azide (2,100 cm$^{-1}$) was no longer detectable in the IR spectrum of a sample (1–2 hours). The solvent was stripped off in vacuo, the residue was dissolved in 20 ml of dry chloroform and 0.48 ml (6.0 millimols) of pyridine, and 1.03 g (6.0 millimols) of phenoxyacetyl chloride in 25 ml of chloroform were added dropwise at −5° C. The reaction mixture was stirred for 1 hour at 20° C., extracted by shaking with phosphate buffer (pH=7) and dried over MgSO$_4$, and the solvent was removed in vacuo and the residue chromatographed over 300 g of silica gel with ethyl acetate/cyclohexane (1:1). Yield: 2.50 g (82%) of a yellow oil as a 1:1 mixture of the diastereomers I (R$_F$=0.41) and B (R$_F$=0.36). A sample of the diastereomer B was obtained in pure form by crystallization from diethyl ether. Melting point 51° C.

IR (CCl$_4$): 3200–3450 (NH), 1770 (C=O-lactam), 1740 (C=O-ester), 1690 (C=O-amido), 1670 cm$^{-1}$ (C=C).

$^1$H—NMR (CDCl$_3$):

R* δ=1.44 and 1.46 (each s; 2CH$_3$), 2.02 (s; SCH$_3$), 4.35 and 4.40 (AB part; ring CH$_2$), 4.48 (s; O—CH$_2$—C=O), 4.53 (s; HC—CO$_2$Bz), 4.77 (dd, J$_1$=2.3 Hz, J$_2$=8.7 Hz; C—3—H), 4.89 (d, J=2.3 Hz; C—4—H), 5.19 (s, broad; CH$_2$-benzyl), 6.46 (s, broad; ring C=C—H), 7.30 (s; C$_6$H$_5$-benzyl), 6.80–7.45 (m; NH, O—C$_6$H$_5$).

S* δ=1.39 and 1.43 (each s; 2CH$_3$), 2.04 (s; SCH$_3$), 4.23 and 4.39 (AB part; ring CH$_2$), 4.46 (s; O—CH$_2$—C=O), 4.53 (s; HC—CO$_2$—Bz), 4.73 (d, J=2.3 Hz; C—4—H), 4.88 (dd, J$_1$=2.3 Hz, J$_2$=8.0 Hz; C—3—H), 5.22 and 5.23 (AB part; CH$_2$-benzyl), 6.55 (s, broad; ring C=C—H), 7.30 (s; C$_6$H$_5$-benzyl), 6.80–7.45 (m; NH, O—C$_6$H$_5$).

$C_{27}H_{30}N_2O_7S$ (526.61) Calculated C 61.58 H 5.74. Found C 61.51 H 5.76

It is understood that the specification and examples are illustrative but not limitative of the present invention and that other embodiments within the spirit and scope of the invention will suggest themselves to those skilled in the art.

We claim:

1. A process for the preparation of a 7-amino-1-dethia-1-oxa-3-hydroxymethyl-cephem-4-carboxylic acid derivative of the formula

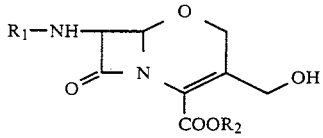 (I)

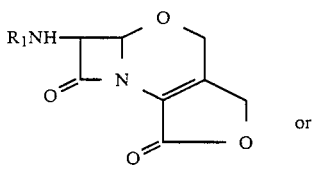 (II)

or

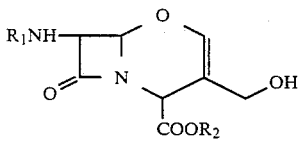 (III)

in which $R_1$ is hydrogen or the acyl radical of an organic carboxylic acid or an optionally substituted protective group Z and $R_2$ is a carboxyl protective group or a pharmaceutically acceptable ester radical, which comprises (a) (i) reacting a compound of the formula

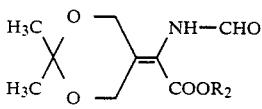 (IV)

with a sulphurization agent thereby to produce a compound of the formula

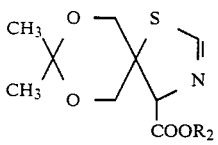 (V)

and reacting the compound of formula (V) with a strong base in a solvent at a low temperature and then with an $R_3$-containing alkylating agent, (ii) or reacting a compound of the formula

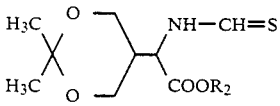 (IV')

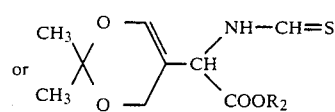 (IV")

with an alkylating agent, thereby to produce a compound of the formula, these compounds are then

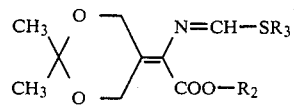 (VI)

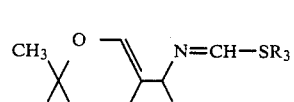 (VI')

or (b) reacting the compound VI or VI' with an activated derivative of an acid of the formula $$X-CH_2-COOH \quad (VII)$$

in which

X is azido or phthalimido, in the presence of a base, in a solvent, to give a compound of the formula

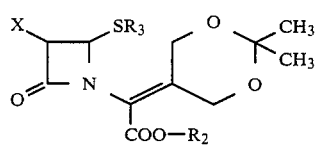 (VIII)

or a double bond isomer thereof of the formula

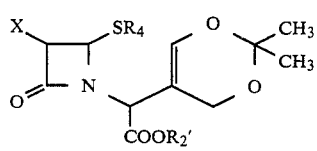 (VIII')

(c) (i) in the case in which X is azido reacting VIII or VIII' with a reducing agent in the presence of an amine, in a solvent, or (ii) in the case in which X is phthalimido, with a phthalimide-cleaving reagent, to give a compound of the formula

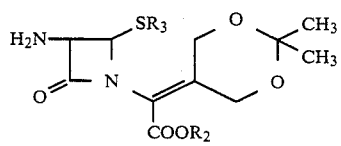 (IX)

or a double bond isomer thereof of the formula

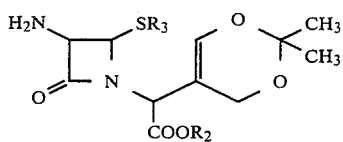 (IX')

(d) reacting IX or IX' with (i) a carboxyl-activated carboxylic acid $R_1'$—COOH in which $R_1'$ is an organic radical or with (ii) a reagent which is capable of introducing the optionally substituted Z protective group, to give a compound of the formula

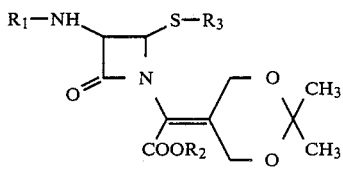

or a double bond isomer thereof of the formula (X')

(e) and reacting the compound of the formula (X) or (X') with a chlorinating agent in a solvent which is inert to chlorination, and then with a protic acid or with a Lewis acid.

2. A process according to claim 1, wherein the sulphurization agent for the conversion of the compound (IV) to the compound (V) is Lawesson reagent.

3. A process according to claim 1, wherein the strong base in reaction step (a) is butyl-lithium.

4. A process according to claim 1, wherein the alkylating agent in reaction step (a) is methyl iodide.

5. A process according to claim 1, wherein the chlorinating agent in reaction step (e) is chlorine or sulphuryl chloride.

* * * * *

UNITED STATES PATENT AND TRADEMARK OFFICE
CERTIFICATE OF CORRECTION

PATENT NO. : 4,496,723

DATED : January 29, 1985

INVENTOR(S) : Dieter Hoppe, et al.

It is certified that error appears in the above-identified patent and that said Letters Patent is hereby corrected as shown below:

| | |
|---|---|
| Col. 5, line 15 | Middle of formula delete "$COOR_2$," and substitute --$COOR_2$-- |
| Col. 6, line 43, Formula "(XII)" | Middle of formula delete "$COOCH_3$" and substitute --$COOCH_2$-- |
| Col. 14, line 47 and Col. 17, line 60 | Delete beginning of formula and substitute: 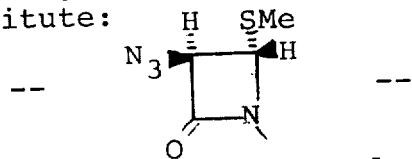 |
| Col. 15, line 23 | Delete beginning of formula and substitute: 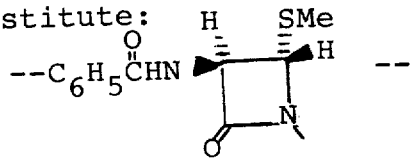 |
| Col. 16, line 8 | Delete middle of formula and substitute: 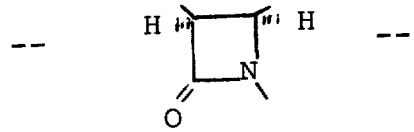 |
| Col. 16, line 16 | After "4" insert -- - -- |
| Col. 16, line 53 | Delete beginning of first formula and substitute: 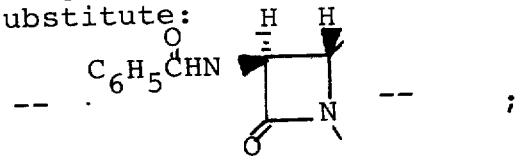 ; delete middle of second formula and substitute: |

UNITED STATES PATENT AND TRADEMARK OFFICE
CERTIFICATE OF CORRECTION

PATENT NO. : 4,496,723

DATED : January 29, 1985

INVENTOR(S) : Dieter Hoppe, et al.

It is certified that error appears in the above-identified patent and that said Letters Patent is hereby corrected as shown below:

Col. 17, line 35     Delete beginning of formula and substitute: 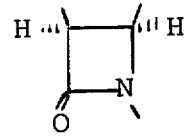 -- 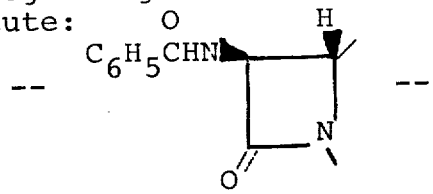 --

Col. 19, line 7     After "Hz" delete "," and substitute --;--

Col. 19, line 15     Delete beginning of first formula and substitute:  ; delete second formula and substitute -- 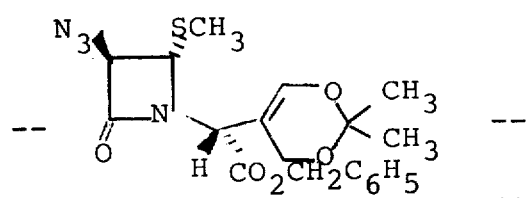 --

Col. 20, line 9     Delete beginning of first formula and substitute: 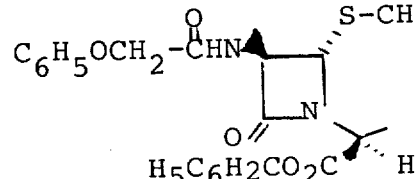 ;

UNITED STATES PATENT AND TRADEMARK OFFICE
CERTIFICATE OF CORRECTION

PATENT NO. : 4,496,723
DATED : January 29, 1985
INVENTOR(S) : Dieter Hoppe, et al.

It is certified that error appears in the above-identified patent and that said Letters Patent is hereby corrected as shown below:

delete beginning of second formula and substitute:

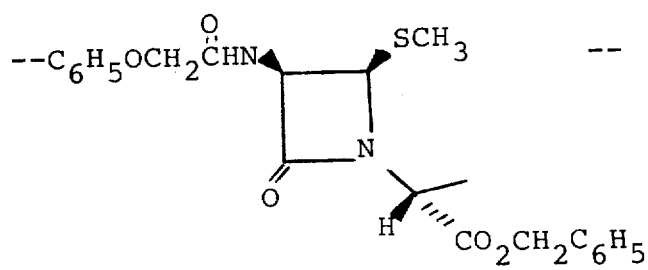

Col. 22, line 17    Insert --or--

Col. 22, line 25    Delete "or"

Signed and Sealed this

Twenty-fourth Day of September 1985

[SEAL]

Attest:

Attesting Officer

DONALD J. QUIGG

Commissioner of Patents and Trademarks—Designate